(12) United States Patent
Hansson

(10) Patent No.: US 6,814,721 B1
(45) Date of Patent: Nov. 9, 2004

(54) ABSORBENT ARTICLE WITH FLUID IMPERMEABLE BACKSHEET PORTION BENEATH MAIN ABSORPTION AREA AND METHOD OF PRODUCING

(75) Inventor: Roy Hansson, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 341 days.

(21) Appl. No.: 10/130,248

(22) PCT Filed: Nov. 17, 2000

(86) PCT No.: PCT/SE00/02259
§ 371 (c)(1),
(2), (4) Date: May 16, 2002

(87) PCT Pub. No.: WO01/35890
PCT Pub. Date: May 25, 2001

(30) Foreign Application Priority Data

Nov. 18, 1999 (SE) .............................. 9904202

(51) Int. Cl.[7] .............................................. A61F 13/15
(52) U.S. Cl. .................................. 604/385.01; 604/374
(58) Field of Search ........................... 604/374, 385.01, 604/358.23, 380, 381, 385.17, 385.03, 387

(56) References Cited

U.S. PATENT DOCUMENTS

| | | | |
|---|---|---|---|
| 3,763,863 A | * 10/1973 | Mesek et al. ................ | 604/365 |
| 3,844,288 A | * 10/1974 | Kiela ........................... | 604/379 |
| 4,713,069 A | 12/1987 | Wang et al. | |
| 5,423,787 A | * 6/1995 | Kjellberg .................... | 604/368 |
| 5,718,698 A | 2/1998 | Dobrin et al. | |
| 6,410,822 B1 | * 6/2002 | Mizutani .................... | 604/380 |
| 6,486,379 B1 | * 11/2002 | Chen et al. ................. | 604/378 |
| 6,492,574 B1 | * 12/2002 | Chen et al. ................. | 604/378 |
| 6,503,233 B1 | * 1/2003 | Chen et al. ............ | 604/385.01 |
| 6,575,948 B1 | * 6/2003 | Kashiwagi et al. ... | 604/385.101 |
| 6,703,538 B2 | * 3/2004 | Lassen et al. ............... | 604/378 |
| 2001/0047159 A1 | * 11/2001 | Mizutani ............... | 604/385.23 |
| 2003/0083632 A1 | * 5/2003 | Rubio .................... | 604/385.01 |
| 2004/0039362 A1 | * 2/2004 | Roe et al. .............. | 604/385.01 |

FOREIGN PATENT DOCUMENTS

| | | |
|---|---|---|
| EP | 0 025 315 B2 | 3/1981 |
| EP | 0 710 472 A1 | 5/1996 |
| EP | 0 813 848 A1 | 12/1997 |
| EP | 0 813 849 A1 | 12/1997 |
| SE | 512 365 | 3/2000 |
| SE | 9803981 | 5/2000 |
| SE | 514 136 | 1/2001 |
| WO | 95/09592 | 4/1995 |
| WO | 97/39713 | 10/1997 |
| WO | 00/02727 | 1/2000 |

* cited by examiner

Primary Examiner—John J. Calvert
Assistant Examiner—Michael Bogart
(74) Attorney, Agent, or Firm—Burns, Doane, Swecker & Mathis, L.L.P.

(57) ABSTRACT

The invention relates to an absorbent product with a longitudinal direction and a transverse direction, two side edges (109, 110) extending essentially in the longitudinal direction, a front portion (114), a rear portion (115), a first surface and a second surface, and an absorption body (105) arranged between the first surface and the second surface. The absorption body (105) has a liquid storage area (106), and a secondary absorption area (107), the secondary absorption area (107) comprising portions which completely surround the liquid storage area (106) in the plane of the product, the liquid storage area (106) accounting for at least 75% of the total absorption capacity of the product, and a liquid-impermeable material layer (104) being arranged on the second surface of the product and essentially only within the liquid storage area.

The invention also relates to a method of producing the absorbent product.

12 Claims, 2 Drawing Sheets

ABSORBENT ARTICLE WITH FLUID IMPERMEABLE BACKSHEET PORTION BENEATH MAIN ABSORPTION AREA AND METHOD OF PRODUCING

TECHNICAL FIELD

The invention relates to an absorbent product such as a sanitary towel, a panty liner or an incontinence pad with a longitudinal direction and a transverse direction, two side edges extending essentially in the longitudinal direction, a front portion, a rear portion, a first surface and a second surface, and an absorption body arranged between the first surface and the second surface. The invention also comprises a method of producing such a product.

BACKGROUND ART

Absorbent products of the type referred to in the introduction are in most cases provided with a liquid-blocking rear-side layer, usually a thin liquidtight plastic film layer. An associated problem, however, is that the products feel moist and uncomfortable to wear. The moisture can also cause inconvenience in the form of unpleasant odour and skin irritation. It has therefore become more usual to provide absorbent products with breathable liquid-blocking layers, for example microporous plastic films, or impermeable nonwoven materials. Examples of breathable materials are given in EP 813 848, EP 813 849, EP 710 472, EP 25 315 and U.S. Pat. No. 4,713,069. Such breathable barrier layers do not, however, have an adequate liquid-blocking effect and are therefore in practice used virtually exclusively in panty liners, where the quantity of liquid absorbed is very small. Sanitary towels and incontinence pads, which are expected to absorb considerably greater quantities of liquid, therefore continue to be provided with completely liquidtight barrier layers. There is consequently still a need for improved breathability in absorbent products such as sanitary towels, panty liners and incontinence pads.

Absorbent products such as sanitary towels, panty liners and incontinence pads are intended to be worn in close contact with the body of the wearer. In this connection, such an absorbent product is usually arranged inside the briefs of the wearer and is kept in contact with the body during use by pressure from the briefs. However, it has become much more common for women to wear what are known as thongs, that is to say briefs in which the rear part of the crotch portion is very narrow. In this connection, sanitary towels, panty liners and incontinence pads which are designed to fit in conventional briefs have proved to be virtually impossible to fasten in a thong in such a manner that the towel or the panty liner sits correctly in relation to the body of the wearer and is held in position throughout use. Furthermore, thongs are often worn for aesthetic reasons because they are virtually invisible even under clinging clothes and. do not give rise to unsightly edge lines or creases in the clothes. With a conventional absorbent product, which projects beyond the edges of the thong, a large part of the desired aesthetic effect of wearing a thong is of course lost. Absorbent products have therefore been produced, which are adapted to the shape of a thong. Such absorbent products are described in SE 9803981-1, WO 97/39713 and SE 9901758-4. However, the special essentially triangular shape with a very narrow rear portion, which is necessary in order that a product can fit in a thong, means that the surface area available for absorption is relatively small. The risk of leakage is then great if the product cannot catch and absorb all the bodily fluid discharged.

One object of the invention is therefore to provide a breathable absorbent product with an improved liquid-absorption capacity. Another object of the invention is to provide a breathable absorbent product with a high degree of leakproofness. A further object of the invention is to provide a breathable absorbent product which is suitable for use with a thong.

DISCLOSURE OF INVENTION

By means of the present invention, an absorbent product of the type mentioned in the introduction has been produced, which product essentially eliminates the difficulties mentioned above. A product according to the invention is characterized mainly in that the absorption body has a liquid storage area, and a secondary absorption area, the secondary absorption area comprising portions which completely surround the liquid storage area in the plane of the product, the liquid storage area accounting for at least 75% of the total absorption capacity of the product, and a liquid-impermeable material layer being arranged on the second surface of the product and essentially only within the liquid storage area.

By concentrating the absorption capacity in a primary liquid absorption area where liquid can be absorbed and stored, it is possible to limit and control the spread of liquid in the absorbent product. As a result, it is also possible to limit the extent of the liquidtight barrier layer of the product to this area because other parts of the product are expected to absorb only extremely small quantities of liquid.

It is advantageous if the liquid storage area consists essentially of a more fine-capillary and/or more hydrophilic material than the secondary absorption area, or if the liquid storage area comprises superabsorbents, because this means that liquid will be transported in the direction from the secondary absorption area to the liquid storage area and not in the opposite direction. As a result, the edges of the liquid storage area also function as liquid transport barriers, so that liquid will not pass from the liquid storage area to the fluffier and/or less hydrophilic secondary absorption area until the liquid storage area is saturated with liquid.

It has been found that absorbent products worn with thongs stay in place surprisingly well and it is therefore to a great extent possible to predict where wetting and absorption will take place. The present invention exploits this fact to produce a central liquid absorption area with, in relation to the rest of the product, a great absorption capacity and a high degree of leakproofness.

According to one embodiment of the invention, the absorbent product is of essentially triangular plane shape, with a narrower rear portion than front portion. Such a shape makes the product particularly suitable for use together with a thong.

The absorbent product can also be provided with a liquid-permeable rear-side layer which is arranged on the second surface of the product, that is to say the surface intended to face the underwear of the wearer during use of the product. In this connection, the liquid-impermeable material layer is arranged between the liquid storage area of the absorption body and the liquid-permeable rear-side layer. Such a liquid-permeable rear-side layer suitably comprises a nonwoven layer which gives the outside of the product a textile nature. A textile rear side on the product has a number of advantages, such as great comfort, good friction and thus better retention in the underwear, and an attractive appearance.

According to one embodiment of the invention, the, liquid-impermeable material layer is connected to the liquid storage area of the absorption body on that surface of the liquid storage area which is intended to face away from the wearer when the product is in use. Such an embodiment makes it possible to handle the combination of liquid storage material and barrier layer as a single component in a production process.

The liquid storage area should have a great absorption capacity and a good capacity for spreading and storing liquid. In this connection, it is advantageous if the liquid storage area comprises a layer of cellulose fibres with a density of at least 150 g/m$^3$ and preferably a layer suitably of dry-formed cellulose fibres with a density of at least 250 g/m$^3$.

A material which has been found to be suitable for the secondary absorption area comprises a layer of bound cellulose-fibre-based material with a density of at most 125 g/m$^3$ which is arranged on the first surface of the product and extends over the liquid storage area and beyond the edges of the liquid storage area around the entire periphery of the liquid storage area. Alternatively, the secondary absorption material is arranged only around the periphery of the liquid storage area. In this context, a bound material means a material which has been treated with a binder so as to stabilize the fibrous structure in the layer. Accordingly, the material can be bound using latex and/or binding fibres.

According to one embodiment. of the invention, the rear-side material consists of a breathable material with a great capacity to resist liquid penetration.

According to another embodiment, the liquid storage area has an absorption capacity accounting for at least 85% of the total absorption capacity of the product.

The product can also have an adhesive fastening means which is arranged on the rear-side material and allows the passage of gas and water vapour within the area of the secondary absorption area.

The invention also comprises a method of producing an absorbent product according to Patent Claim 1. The method comprises a continuous web of absorbent material being laminated by a first surface to a liquidtight material layer, after which liquid storage areas are clipped or cut from the laminate of absorbent material and liquidtight material, and a continuous web of secondary absorption material being joined to a second surface of the punched-out liquid storage areas so that these are completely surrounded by the secondary absorption material in the plane of the material web, after which absorbent products are clipped or cut from the finished laminate.

According to one embodiment of the invention, a covering of liquid-permeable material is fastened to at least one surface on the laminate of secondary absorption material and liquid storage areas before the absorbent products are cut out of the finished laminate.

BRIEF DESCRIPTION OF DRAWINGS

The invention is described in greater detail below with reference to the exemplary embodiments shown in the appended drawings, in which.

MODE(S) FOR CARRYING OUT THE INVENTION

Figure 1:
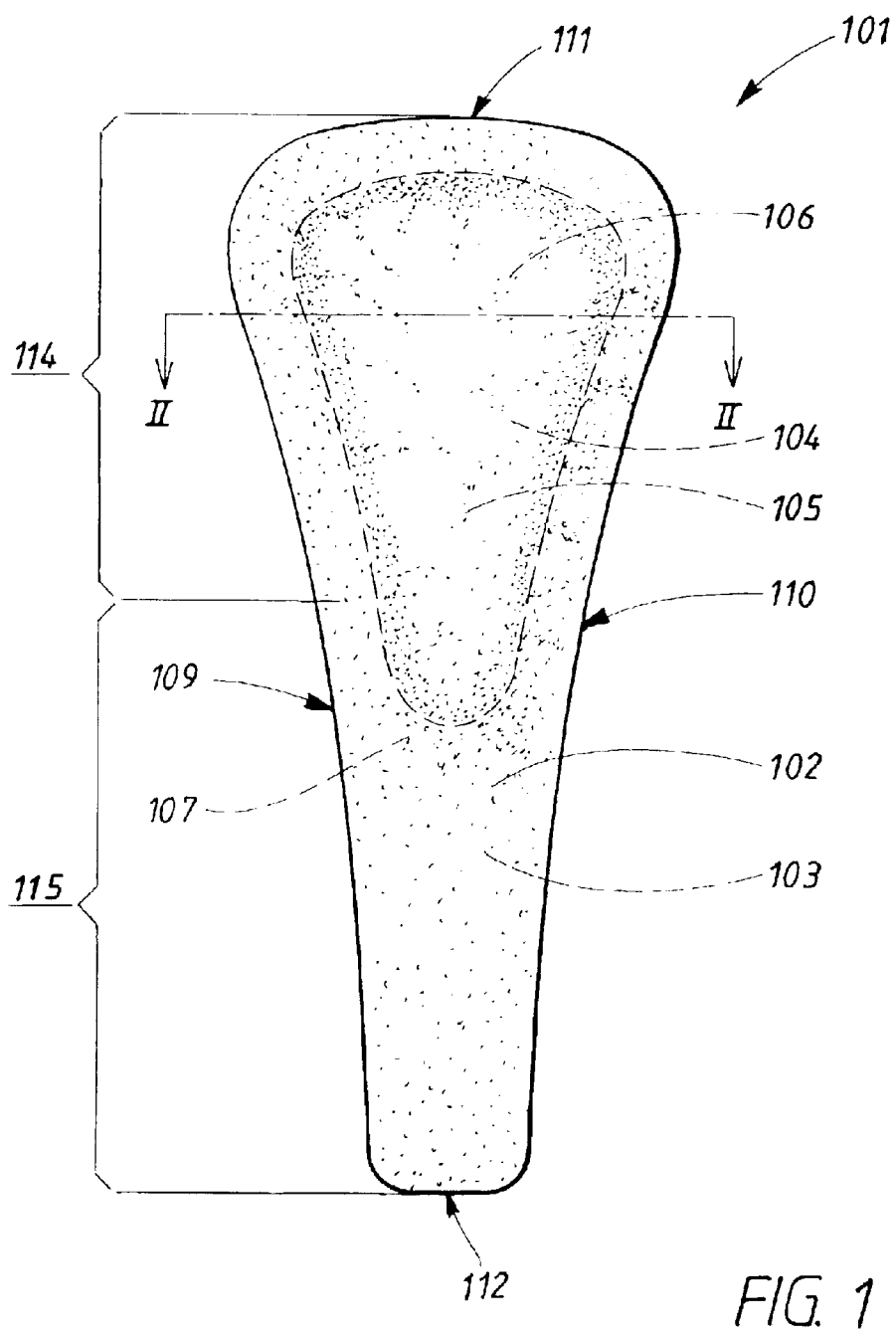
FIG. 1 shows a sanitary towel according to a first embodiment of the invention.
Figure 2:
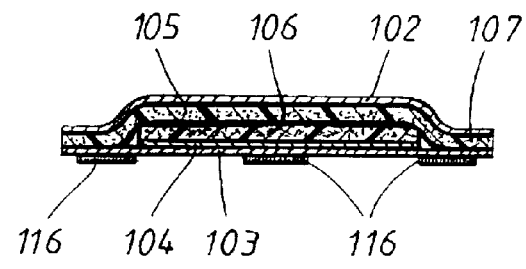
FIG. 2 shows a section along the line II—II through the sanitary towel in FIG. 1.

The sanitary towel 101 shown in FIGS. 1 and 2 comprises a liquid-permeable surface layer 102 arranged on that side of the sanitary towel which is intended to face a wearer during use, a liquid-permeable rear-side layer 103 arranged on that side of the sanitary towel which is intended to face away from the wearer during use, and an absorption body 105 enclosed between the two surface layers 102, 103. A liquid barrier layer 104 is also arranged between the absorption body and the rear-side layer 103.

The liquid-permeable surface layer 102 is the same shape and size as the absorption body 105. The rear-side layer 103 is also shaped like the absorption body. The surface layers 102, 103 are connected to the absorption body 105, for example by gluing, needling, sewing, or by welding using heat or ultrasound.

The liquid-permeable surface layer 102 is of conventional type and can therefore consist of any liquid-permeable material suitable for the purpose. Examples of such material are different types of thin nonwoven material, perforated plastic films, net material, liquid-permeable foam material or the like. The liquid-permeable surface layer 102 can be constructed from two or more different materials in order to provide different functions of the surface layer. For example, it is usual to arrange a liquid-transporting layer inside a liquid-admission layer. It is also known to arrange different types of material on different parts of that surface on the sanitary towel which faces the wearer during use. A material with good admission capacity can therefore advantageously be arranged in that portion of the sanitary towel which is expected to be moistened first by the major part of the bodily fluid, while portions of the surface layer which are in the first instance to constitute a contact surface against the body of the wearer are provided with a material which has been optimized with regard to softness and kindness to the skin.

It is not necessary either for the invention that the liquid-permeable surface layer 102 consists of a separate material layer, but the surface layer 102 can be a surface on the absorption body 105 of the sanitary towel 101.

The liquid-permeable rear-side layer 103 can also consist of any suitable liquid-permeable material. Particularly advantageous materials are soft nonwoven materials which provide a soft skin-friendly textile surface. The use of a textile surface material affords a number of advantages, such as a high degree of wearer comfort, high friction and thus better retention in a pair of briefs, and an aesthetically attractive appearance.

The liquid barrier layer 104 is a layer of liquidtight material. Examples of such material layers are thin plastic films and coatings of resin, wax, liquidtight adhesive or the like.

The absorption body 105 consists of two parts, a first part which constitutes the liquid storage area 106 of the absorption body 105, and a second part which is relatively thin and is in the form of one or more material layers which extend over essentially the entire surface of the sanitary towel. During use of the sanitary towel 101, it is arranged in the genital area of the wearer, with a portion located in the region of the vaginal orifice of the wearer. As a result, discharged bodily fluid will meet the sanitary towel 101 within a limited and to a great extent predetermined area on the sanitary towel, what is known as the wetting area. The positioning of the liquid storage area 106 is selected in such a manner that it coincides with the anticipated wetting area of the sanitary towel 101. The liquid storage area 106 is therefore considerably smaller in area than the sanitary towel as a whole. By virtue of the fact that the liquid storage area 106 is positioned in the wetting area of the sanitary towel, however, essentially all the bodily fluid discharged into the sanitary towel will still pass into and be absorbed in the liquid storage area 106. It is therefore of utmost importance that the liquid storage area 106 has sufficient absorption capacity to be capable of absorbing the expected quantity of bodily fluid. In this connection, the absorption capacity in the liquid storage area 106 is to be at least 75%, and preferably at least 85%, of the total absorption capacity of the sanitary towel. It is usually estimated that a panty liner should have an absorption capacity of roughly 3–5 ml and a sanitary towel should be capable of absorbing roughly 12–15 ml. For products intended for night use, for example, or for incontinence pads, an even greater absorption capacity may be desirable.

The second part of the absorption body 105 is arranged as a layer between the liquid-permeable surface layer 102 and the liquid storage area 106 and serves as a liquid-transfer layer between the liquid-permeable surface layer 102 and the first part of the absorption body in the liquid storage area 106. The second part of the absorption body 105 also extends beyond the edges of the liquid storage area 106 in the plane of the product, around the entire periphery of the liquid storage area 106, and then constitutes a secondary absorption area 107 around the liquid storage area 106.

Suitable absorbent materials for use in the absorption body 105 are, for example, cellulose fluff pulp, absorbent bound fibre layers, tissue layers, absorbent foam, peat or the like. The absorption body can also contain superabsorbent polymers, that is to say polymers with the capacity to absorb several times their own weight of liquid, forming a liquid-containing gel. Superabsorbents are usually in the form of particles, flakes, fibres, granules or the like. The superabsorbent material can be used on its own or together with other absorbent material.

The materials in the liquid storage area 106 and, respectively, the secondary absorption area 107 are advantageously selected in such a manner that the liquid storage area is more fine-capillary and/or has greater hydrophilicity than the secondary absorption area 107. A fine-capillary material can be produced by, for example, compressing a porous, compressible structure, such as a fibre wadding, or by selecting a material with small pores. Generally, it can be said that fibrous structures with a large proportion of thin fibres have finer capillaries than fibrous structures with a large proportion of thick fibres. It is also possible to use what are known as capillary fibres, that is to say fibres with external capillaries, in order to produce a highly capillary material. In a corresponding manner, a difference in hydrophilicity can be obtained either by treating the material chemically or physically or by selecting materials which have different hydrophilicity from the outset.

In order to achieve the desired effect of rapid liquid admission to the liquid storage area 106, great absorption capacity and liquid-retaining capacity in the liquid storage area 106, as well as little or no spread of absorbed liquid to the secondary absorption area 107, it is therefore suitable for the liquid storage area 106 to comprise hydrophilic material with a great absorption capacity, such as cellulose fibres, superabsorbent material or the like, while, the material in the secondary absorption area 107 can be selected from materials with a low, or very low absorption capacity, for example fibre wadding made of synthetic fibres. A material which has been found to function particularly well as absorption material in the liquid storage area is the dry-formed cellulose fibrous material described in WO 94/10956. A material which has proved to function particularly well as secondary absorption material is a bulky airlaid latex-bound cellulose-fibre-based material with a density of at most 125 g/m$^3$.

As mentioned, the secondary absorption area 107 surrounds the liquid storage area 106 around its entire periphery. As a result, the secondary absorption area 107 forms a safety zone which can catch and absorb small quantities of liquid, or individual drops of liquid, which meet the sanitary towel outside the wetting area. Owing to its low liquid-transport capacity, the secondary absorption area 107 also prevents liquid reaching the edges of the sanitary towel and causing leakage. As the liquid storage area 106 has to have a great absorption capacity in relation to its area, this area usually has relatively great rigidity. The secondary absorption area 107 then serves the additional purpose of constituting a soft cushioning between the liquid storage area 106 and the body of the wearer.

It may also be suitable to make liquid transport in the plane of the sanitary towel even more difficult by providing the sanitary towel with some form of liquid barrier which prevents liquid being transported in the absorption material or in the liquid-permeable surface layer 102 to the very edges of the sanitary towel. Examples of such liquid barriers are compressions, welds, strands of adhesive, folded-over plastic strips or means of rendering materials hydrophobic, such as wax or the like. In this connection, the liquid barriers can be arranged along the edges of the sanitary towel and/or along the edges on the liquid storage area 106.

The sanitary towel 101 is designed with a relatively wide front portion 114 and a considerably narrower rear portion 115. The sanitary towel 101 also has two side edges 109, 110, the main extent of which is in the longitudinal direction of the sanitary towel, and an essentially transverse front edge 111 and a likewise transverse rear edge 112.

During use of the sanitary towel 101, the front portion 114 is that part of the sanitary towel which faces forwards on the wearer and will then be arranged over the genitals of the wearer. The front portion 114 narrows in the direction towards the rear portion 115 which is considerably narrower than the front portion 114.

In order that the sanitary towel does not extend so far back during use that it is conspicuous when it is worn together with a thong, it is suitable for the rear portion of the sanitary towel to have a length of between 80 mm and 140 mm and for the total length of the sanitary towel not to exceed roughly 260 mm.

In order to fasten the sanitary towel in a pair of briefs, a fastening means 116 is arranged on the outside of the rear-side layer 103 of the sanitary towel. The fastening means 116 is in the form of longitudinal strips of self-adhesive glue. Before use, the fastening means 116 is protected in a conventional manner, for example by being covered by a protective layer of paper or plastic treated with silicone or stamped so as to be easily detachable from the adhesive when the sanitary towel is to be used. The adhesive can of course be arranged in any pattern suitable for the purpose. In order to minimize the effect of the adhesive on the breathability of the sanitary towel within the secondary absorption area, it is suitable for as little adhesive as possible to be arranged within this area, or for the adhesive to be arranged in a discontinuous pattern which allows intermediate, exposed portions of the rear-side layer 103 to breathe. Alternatively, a breathable fastening adhesive can be used, at least within the secondary absorption area 107.

Other types of fastening means can also be used, such as friction coatings, press-studs, clips, fastening flaps or the like. Another alternative is fastening adhesive which is attached to the body of the wearer. Different types of fastening arrangements can also be combined with one another. It is common, for example, to provide a sanitary towel with both fastening adhesive on the rear-side layer and with fastening flaps.

The sanitary towel 101 shown in FIGS. 1 and 2 can be produced efficiently and economically from continuous material webs by laminating an absorbent material layer to a liquidtight barrier layer, after which liquid storage areas with the associated liquid barrier layer are clipped or cut out of the laminate web and joined to the other components of the sanitary towel.

Figure 3:
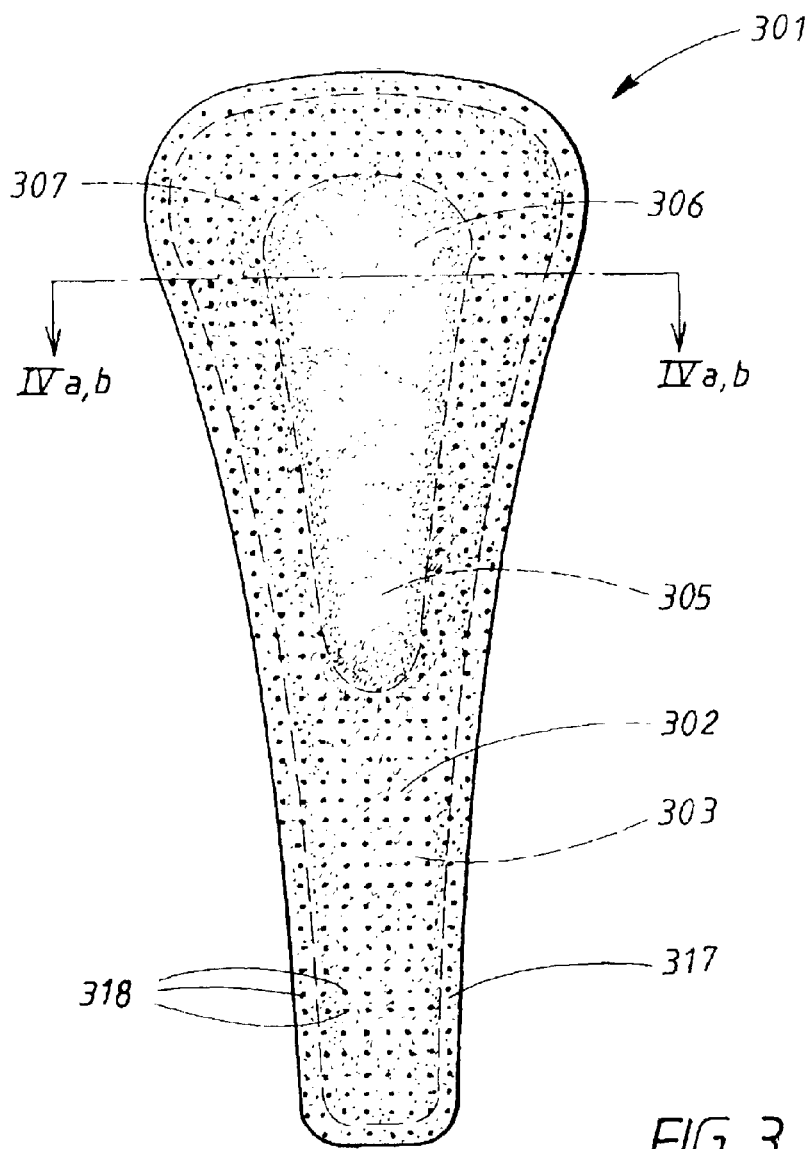
FIG. 3 shows a sanitary towel according to a second embodiment of the invention.

FIGS. 3 and 4 show a sanitary towel 301 comprising a liquid-permeable surface layer 302, a rear-side layer 303 and an absorption body 305 enclosed between the surface layers 302, 303. The surface layers 302, 303 are interconnected within an edge portion 317 projecting around the absorption body 305. Such an edge join can be produced in a conventional manner by gluing, sewing, or welding using heat or ultrasound.

The liquid-permeable surface layer 302 can, as described in connection with FIGS. 1 and 2, consist of any liquid-permeable material suitable for the purpose.

The rear-side layer 303 consists of a layer of liquidtight material. Examples of such materials are different types of thin plastic films, or nonwoven material treated so as to resist liquid penetration, for example by coating with plastic, wax or the like. The liquidtight rear-side layer 303 can also consist of a liquidtight surface on the absorption body 305. In such an embodiment, however, the rear-side layer cannot be joined to the liquid-permeable surface layer 302 in an edge join around the absorption body 305, but the sanitary towel 301 then has a construction similar to that described in connection with the sanitary towel 101 in FIGS. 1 and 2.

Figure 4A:
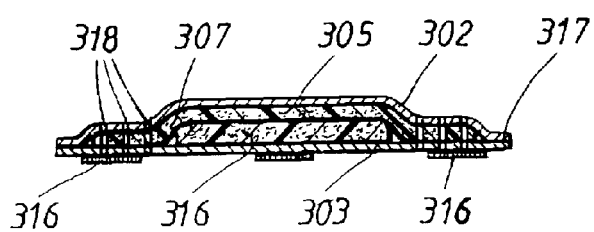
FIG. 4 shows a section along the line IV—IV through the sanitary towel in FIG. 3.
Figure 4B:
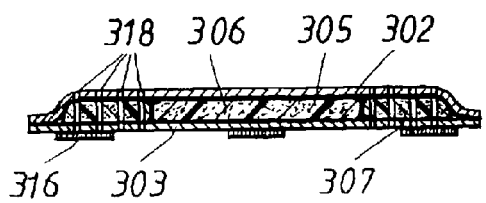

In the embodiment shown in FIG. 4a, the absorption body 305 has the same construction as the absorption body 105 shown in FIGS. 1 and 2. The absorption body 305 therefore comprises a liquid storage area 306, and a secondary absorption area 307, the secondary absorption area being arranged in the form of a material layer which also extends between the liquid-permeable surface layer 302 and the liquid storage area 306. FIG. 4b shows an alternative embodiment in which the secondary absorption area is arranged only in the same plane as the liquid storage area 306 and completely surrounds the liquid storage area in the plane.

Although the absorption body 305 in the figures is shown as being constructed from two separate parts, it is possible to make the absorption body 305 from a single absorption layer which is imparted greater hydrophilicity and/or more compact structure within the liquid storage area 306. Greater absorption capacity within the liquid storage area 306 can also be brought about by means of an accumulation of absorption material within this area and/or addition of superabsorbents.

In order to make the sanitary towel 301 breathable within those portions of the secondary absorption area 307 located around the periphery of the liquid storage area 306, these have been provided with perforations 318 which, in FIGS. 4a and 4b, extend through the entire thickness of the sanitary towel. Alternatively, the perforations 318 can be arranged through only a part of the thickness of the sanitary towel 301 as long as at least the liquidtight rear-side layer 303 is perforated. In this connection, the perforations 318 can be produced by, for example, needling, stamping, punching or the like. By perforating a border around the liquid storage area 306, a sanitary towel is therefore obtained with a central liquidtight absorption portion and a surrounding breathable safety zone.

Like the sanitary towel 101 in FIGS. 1 and 2, the sanitary towel shown in FIGS. 3 and 4 is provided with fastening means in the form of strands 316 of adhesive arranged on the liquidtight rear-side layer 303.

Although the invention is described above in connection with sanitary towels, it can of course also be applied to absorbent products such as incontinence pads and panty liners.

What is claimed is:

1. An absorbent product with a longitudinal direction and a transverse direction, two side edges extending essentially in the longitudinal direction, a front portion, a rear portion, a first surface and a second surface, and an absorption body arranged between the first surface and the second surface, the absorption body has a liquid storage area, and a secondary absorption area, the secondary absorption area comprising portions which completely surround the liquid storage area in the plane of the product, the liquid storage area accounting for at least 75% of the total absorption capacity of the product, and a liquid-impermeable material layer being arranged on the second surface of the product and essentially only within the liquid storage area.

2. Absorbent product according to claim 1, wherein the product is of essentially triangular plane shape, with a narrower rear portion than front portion.

3. Absorbent product according to claim 1, wherein a liquid-permeable rear-side layer is arranged on the second surface of the product, the liquid-impermeable material layer being arranged between the liquid storage area of the absorption body and the liquid-permeable rear-side layer.

4. Absorbent product according to claim 3, wherein the liquid-permeable rear-side layer comprises a nonwoven layer.

5. Absorbent product according to claim 1, wherein the liquid-impermeable material layer is connected to the liquid storage area of the absorption body.

6. Absorbent product according to claim 1, wherein the liquid storage area comprises a layer of dry-formed cellulose fibers with a density of at least 250 g/m$^3$.

7. Absorbent product according to claim 1, wherein the secondary absorption area comprises a layer of bound cellulose-fibre-based material with a density of at most 125 g/m$^3$ which is arranged on the first surface of the product and extends over the liquid storage area and beyond the edges of the liquid storage area around the entire periphery of the liquid storage area.

8. Absorbent product according to claim 3, wherein the rear-side material consists of a breathable material with a great capacity to resist liquid penetration.

9. Absorbent product according to claim 1, wherein the liquid storage area has an absorption capacity accounting for 85% of the total absorption capacity of the product.

10. Absorbent product according to claim 1, wherein an adhesive fastening means is arranged on the rear-side material and allows the passage of gas and water vapor within the area of the secondary absorption area.

11. A method of producing an absorbent product, wherein the method comprises laminating a first surface of a continuous web of absorbent material to a liquidtight material layer, after which clipping or cutting liquid storage areas from the laminate of absorbent material and liquidtight material, and joining a continuous web of secondary absorption material to a second surface of the clipped out or cut out liquid storage areas so that these are completely surrounded by the secondary absorption material in the plane of the material web, after which clipping or cutting absorbent products from the finished laminate.

12. Method according to claim 11, wherein a covering of liquid-permeable material is fastened to at least one surface on the laminate of secondary absorption material and liquid storage areas before the absorbent products are cut out of the finished laminate.

* * * * *